United States Patent
Sarkar et al.

(10) Patent No.: US 9,895,306 B2
(45) Date of Patent: *Feb. 20, 2018

(54) PERSONAL CARE COMPOSITIONS CONTAINING END-FUNCTIONALIZED IONIC SILICONE

(71) Applicant: Momentive Performance Materials Inc., Waterford, NY (US)

(72) Inventors: Alok Sarkar, Malda (IN); Anubhav Saxena, Bangalore (IN); Sandip Tiwari, Bangalore (IN); Benjamin Falk, Yorktown Heights, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/733,482

(22) Filed: Jan. 3, 2013

(65) Prior Publication Data

US 2013/0171080 A1 Jul. 4, 2013

Related U.S. Application Data

(60) Provisional application No. 61/582,914, filed on Jan. 4, 2012.

(51) Int. Cl.
| | |
|---|---|
| *A61K 8/899* | (2006.01) |
| *A61Q 19/00* | (2006.01) |
| *A61Q 1/04* | (2006.01) |
| *A61Q 5/12* | (2006.01) |
| *A61Q 17/04* | (2006.01) |
| *A61Q 5/06* | (2006.01) |

(52) U.S. Cl.
CPC .............. *A61K 8/899* (2013.01); *A61Q 19/00* (2013.01); *A61K 2800/10* (2013.01); *A61Q 1/04* (2013.01); *A61Q 5/06* (2013.01); *A61Q 5/12* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 6,124,490 A | | 9/2000 | Gormley et al. |
| 2003/0211050 A1* | | 11/2003 | Majeti et al. .................. 424/49 |

FOREIGN PATENT DOCUMENTS

| | | | | |
|---|---|---|---|---|
| EP | 0 017 121 A1 | | 10/1980 | |
| JP | 6247827 A | | 9/1994 | |
| JP | 6247835 | * | 9/1994 | .............. A61K 7/48 |
| JP | 6247835 A | | 9/1994 | |
| JP | H10 273414 K1 | | 10/1998 | |
| WO | 1993/25179 A1 | | 12/1993 | |

OTHER PUBLICATIONS

International Search Report and Written Opinion dated Mar. 15, 2014.

* cited by examiner

*Primary Examiner* — Brian Gulledge
(74) *Attorney, Agent, or Firm* — Joseph S. Ostroff

(57) ABSTRACT

A personal care composition contains at least one personal care component and at least one end-functionalized ionic silicone.

16 Claims, No Drawings

PERSONAL CARE COMPOSITIONS CONTAINING END-FUNCTIONALIZED IONIC SILICONE

This application relates to, and claims the benefit of, provisional U.S. patent application Ser. No. 61/582,914, filed Jan. 4, 2012, the entire contents of which are incorporated by reference herein.

BACKGROUND OF THE INVENTION

The present invention relates to the use of ionic silicones in personal care compositions.

JP 6,247,827 and JP 6,247,835 disclose methods for preparing sulfonate-functionalized silicones and their use in personal care compositions. However, these methods do not disclose the incorporation of end-functionalized ionic silicones in personal care compositions.

SUMMARY OF THE INVENTION

A personal care composition is provided which contains at least one personal care component and at least one end-functionalized ionic silicone of the formula:

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ in which:
$R^1, R^2, R^3, R^5, R^6, R^8, R^9, R^{10}, R^{11}, R^{13}, R^{15}$ and $R^{16}$ each independently is an aliphatic, aromatic or fluoro monovalent hydrocarbon group having from 1 to 60 carbon atoms;

$R^4$, $R^{12}$ and $R^{17}$ each independently is a monovalent group bearing ion-pairs and having the formula -A-$I^{x-}M_n^{y+}$, or zwitterion having the formula —R'—$N^+(R'')_2$—R'''—$I^-$, in which A is a spacing moiety having at least one spacing atom, the spacing moiety being selected from the group consisting of divalent hydrocarbon group and hydrocarbonoxy group, I is an ionic group, R' is a divalent hydrocarbon group having from 1 to 20 carbon atoms, R" is a monovalent hydrocarbon group having from 1 to 20 carbon atoms, R''' is a divalent hydrocarbon group having from 2 to 20 carbon atoms, and each M independently is hydrogen or a cation independently selected from alkali metals, alkali earth metals, transition metals, quaternary ammonium groups and phosphonium groups;

$R^7$, $R^{14}$ and $R^{18}$ each independently is —$CH_2CH(R^{19})$($C_nH_{2n}$)—O—$(C_2H_4O)_o$—$(C_3H_6O)_p$—$(C_4H_8O)_q$— $R^{19}$ in which $R^{19}$ is hydrogen or an $R^1$ group as defined above;

superscripts x and y are positive integers subject to the limitation that x=ny;

each subscript n independently has a value of from 0 to 6 and subscripts o, p and q each independently has a value of from 0 to 1000, subject to the limitation that o+p+q ≥1; and, subscripts a, c, d, e, f, g, h, i and j each independently is zero or a positive integer subject to the limitations that 2≤a+b+c+d+e+f+g+h+i+j≤4500 and b≥2.

DETAILED DESCRIPTION OF PREFERRED EMBODIMENTS

In the specification and claims herein, the following terms and expressions are to be understood as indicated.

As used in the specification and including the appended claims, the singular forms "a," "an," and "the" include the plural, and reference to a particular numerical value includes at least that particular value unless the context clearly indicates otherwise.

Other than in the working examples or where otherwise indicated, numerical values and ranges of numerical values herein whether or not modified by such terms as "about" and "approximately" are to be understood to include the indicated value(s) and value(s) approximate thereto. When such a range is expressed, another embodiment includes from the one particular value and/or to the other particular value. Similarly, when values are expressed as approximations, e.g., by use of the modifier "about," it will be understood that the particular value forms another embodiment.

It will also be understood that any numerical range recited herein is intended to include all sub-ranges within that range.

All methods described herein may be performed in any suitable order unless otherwise indicated or clearly contrary to context. The use herein of any and all examples or exemplification language (e.g., "such as"), is intended merely to better illustrate the invention and does not pose a limitation on the scope of the invention unless otherwise claimed. No language in the specification should be construed as indicating any non-claimed element as essential to the practice of the invention.

As used herein, the terms "comprising," "including," "containing," "characterized by" and grammatical equivalents thereof are inclusive or open-ended terms that do not exclude additional, unrecited elements or method steps and are also to be understood as including the more restrictive terms "consisting of" and "consisting essentially of."

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

End-functionalized ionic silicones (I) of the present invention form aggregates of the ionic groups to ion-rich domains, having dimensions, e.g., from 40 to 200 nm, which serve as ionic filler in the composition. These ionic aggregates act as crosslinks and increase the modulus of the material. In addition to acting as crosslinks, the aggregates also behave as reinforcing filler particles and as such may further increase the modulus of the personal care composition containing them. Moreover, due to the reversible nature of the ionic interactions, when heated to a certain level (e.g., ca. 180° C.) the ionic aggregates disaggregate somewhat to form relatively more thermodynamically stable ionic aggregates upon cooling. As a consequence of this phenomenon, the viscosity of these materials keeps increasing during repeated heating/cooling cycles. In addition, the ionic aggregates can be dissolved in a polar solvent such as water then reformed with the removal of the solvent. The presence of ionic groups also helps to make silicones (I) exceptionally compatible with hydrophilic and lipophilic components commonly utilized in such personal care compositions as moisturizers, sunscreens, and the like.

The foregoing unique physicochemical properties of end-functionalized ionic silicones (I) is believed to play an important role in providing such highly desirable product performance characteristics as high transfer resistance and high gloss in lip color formulations, controlled release of actives and substantives in sunscreen agents and other personal care compositions, and the like.

In end-functionalized ionic silicone (I) herein, each $R^1$, $R^2$, $R^3$, $R^5$, $R^6$, $R^8$, $R^9$, $R^{10}$, $R^{11}$, $R^{13}$, $R^{15}$ and $R^{16}$ group is preferably methyl, ethyl, n-propyl, iso-propyl, n-butyl, isobutyl, tert-butyl, n-pentyl, iso-pentyl, neopentyl, tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals. Representative aromatic groups include phenyl, naphthyl; o-, m- and p-tolyl, xylyl, ethylphenyl and benzyl.

In groups $R^4$, $R^{12}$ and $R^{17}$, divalent hydrocarbon spacing group A of ion-pair -A-$I^{x-}$-$M_n^{y+}$ can be, e.g., an alkylene group such as $-(CHR^{20})_m$ wherein $R^{20}$ is hydrogen or an $R^1$ group as defined above and subscript m is a positive integer ranging from 1 to 100 and preferably from 1 to 20; or an arylene group such as $-(CHR^{21})_kC_6H_4(CH_2)_r-$ $-CH^2CH(R')(CH_2)_kC_6H_4-$ or $-CH_2CH(R^{22})(CH_2)_r$-$C_6H_3R^{23}$ wherein R' is hydrogen or an $R^1$ group as defined above, $R^{21}$ is hydrogen or an $R^1$ group as defined above, $R^{22}$ is hydrogen or an $R^1$ group as defined above, $R^{23}$ is a monovalent radical of from 1 to 20 carbon atoms and subscripts k and r are zero or positive integers subject to the limitation $0 \leq k+r \leq 100$.

Divalent hydrocarbon spacing group A can also be, e.g., a divalent hydrocarbonoxy group such as $-(CHR^{24})_s-$ $(O-CHR^{24}CH_2)_{s'}-O-(CH_2)_t$ wherein $R^{24}$ is hydrogen or an $R^1$ group as defined above, s has a value of from 0 to 50, s' has a value of from 1 to 50 and t has a value of from 0 to 50 subject to the limitation $1 \leq s+s'+t \leq 100$.

$I^-$ in the ion-pair-bearing group and in the zwitterion is preferably an ionic group such as sulfonate $-SO_3^-$, sulfate $-OSO_3^-$, and the like.

Examples of cation $M^+$ include Li, Na, K, Cs, Mg, Ca, Ba, Zn, Cu, Fe, Ni, Ga, Al, Mn, Cr, Ag, Au, Pt, Pd, Ru and Rh.

In the zwitterion, R' is a divalent hydrocarbon radical having from 1 to 20 carbon atoms, e.g., $-(CH_2)_s-$; R'' is a monovalent hydrocarbon radical having from 1 to 20 carbon atoms, e.g., $-CH_2CH_3$; and, R''' is a divalent hydrocarbon radical having from 2 to 20 carbon atoms, e.g., $-(CH_2)_4-$.

In end-functionalized ionic silicone (I), $R^7$, $R^{14}$ and $R^{18}$ each independently is $CH_2CH(R^{19})(C_nH_{2n})-O-$ $(C_2H_4O)_o-(C_3H_6O)_p-(C_4H_8O)_q-R^{19}$ wherein $R^{19}$ is hydrogen or an $R^1$ group as defined above, each subscript n independently has a value of from 0 to 6 and subscripts o, p and q each independently has a value subject to the limitation that $o+p+q \geq 1$.

In end-functionalized ionic silicone (I), subscripts a, c, d, e, f, g, h, i and j each independently is zero or a positive number subject to the limitations that $2 \geq a+b+c+d+e+f+g+h+i+j \geq 4500$, $b \geq 2$. In one embodiment, subscript b is 2; subscripts a, c, e, f, g, h, i, j, k, l and m are 0; subscript d is from 5 to 1000, more preferably from 10 to 500, and most preferably from 10 to 200; $R^5$, $R^6$, $R^{10}$ and $R^{11}$ are methyl or ethyl; $R^{10}$ is $-CH_2CH(H$ or $CH_3)$-A-$SO_3M$; A is a divalent benzyl radical; and, M is Li, Na, K, silver, or a quaternary ammonium group, ammonium salt or phosphonium group.

Examples of ionic silicone (I) include sodium sulfonate-capped polydimethylsiloxane, silver sulfonate-capped polydimethylsiloxane, magnesium sulfonate-capped polydimethylsiloxane, calcium sulfonate-capped polydimethylsiloxane, zinc sulfonate-capped polydimethylsiloxane and triethanolammonium sulfonate-capped polydimethylsilane.

Personal care compositions in accordance with the present invention include, but are not limited to deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations comprising at least one of the foregoing personal care applications.

The personal care composition of the present invention may optionally contain up to 99 parts by weight of one or more other organosiloxane resins. Some useful additional organosiloxane resins include combinations of $R_3SiO_{1/2}$, $R_2SiO$, $RSiO_{3/2}$, and $SiO_2$ units in ratios to each other that satisfy the relationship $R_ySiO_{(4-y)/2}$ where y has a value of from 1.0 to 1.50 and R is a methyl group.

The personal care composition of the present invention may optionally contain up to 90 parts by weight of one or more pigments. Pigments suitable for use herein are all inorganic and organic colors/pigments. These are usually aluminum, barium or calcium salts or lakes. A lake is a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein. Other colors and pigments can also be included in the compositions, such as pearls, titanium oxides, Red 6, Red 21, Blue 1, Orange 5, and Green 5 dyes, chalk, talc, iron oxides and titanated micas.

The personal care composition of the present invention may optionally contain up to 99 parts by weight of one or more known or conventional cosmetically-acceptable organic film former. Examples of useful film-forming agents include natural waxes, polymers such as polyethylene polymers, copolymers of PVP, ethylene vinyl acetate, dimethicone gum, resins such as shellac, polyterpenes, and the like.

The personal care composition of the present invention may optionally include up to 50 parts by weight of blocking and/or absorbing sunscreen agents. Blocking sunscreen agents are generally inorganic, such as various cesium oxides, chromium oxides, cobalt oxides, iron oxides, red petrolatum, silicone- and other treated titanium dioxides, titanium dioxide, zinc oxide, and/or zirconium oxide, $BaTiO_3$, $CaTiO_3$, $SrTiO_3$ and SiC. Absorbing sunscreen agents, which are usually organic species, include, but are not limited to, UV-A absorbers, which generally absorb radiation in the 320 to 400 nm region of the ultraviolet spectrum, e.g., anthranilates, benzophenones and dibenzoyl methanes; and, UV-B absorbers, which generally absorb radiation in the 280 to 320 nm region of the ultraviolet spectrum, e.g., p-aminobenzoic acid derivatives, camphor derivatives, cinnamates and salicylates.

Specific examples of organic sunscreen agents include p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl p-aminobenzoic acid, diethanolamine p-methoxycinnamate, digalloyl trioleate, 2-ethylhexyl-2-cyano-3,3-diphenylacrylate, ethylhexyl p-methoxycinnamate, 2-ethylhexyl salicylate, glyceryl aminobenzoate, homomethyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N,N-trimethyl-4-(2-oxoborn-3-ylidene methyl)anillinium methyl sulfate, aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4' dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo) benzyliden-boman-2-one and soluble salts thereof, 3-(4'-methylbenzylidene)-d,1-camphor, 3-benzylidene-d,1-camphor, benzene 1,4-di(3-methylidene-10-camphosulfonic) acid and salts thereof, urocanic acid, 2,4, 6-tris-(2'-ethylhexyl-1'-oxycarbonyl)-anilinol 1,3,5-triazine, 2-(p-(tert-butylamido)anilinol-4,6-bis-(p-(2'-ethylhexyl 1'-oxycarbonyl)anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden) methylbenzyl acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (drometrizole trisiloxane), solubilized 2,2'-methylene-bis-1,6-(2H-benzotriazol-2-yl)-4-(1,1,3,3-tetramethylbutyl)phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreen agents.

In one embodiment, it has been found that a combination of at least three sunscreen agents is especially effective. In another embodiment, it has been found that a combination of four sunscreen agents is particularly effective, especially where chemical sunscreen agents are used.

The personal care composition herein is specifically formulated for use as a color cosmetic, sunscreen, hair conditioner and a moisturizer. Suitable forms and formulations for such application are known to those of ordinary skill in the art. For example, when formulated for use as a sunscreen, the composition may be in the form of a lamellar emulsion, a microemulsion, or a nanoemulsion. In addition, the emulsion may be a fluid simple emulsion, a fluid multiple emulsion, a rigid simple emulsion, or a rigid multiple emulsion. The simple emulsion or multiple emulsion may comprise a continuous aqueous phase containing dispersed lipid vesicles or oil droplets, or a continuous fatty phase dispersed lipid vesicles or water droplets.

In one embodiment, the sunscreen application is an emulsion having a continuous aqueous phase, and may be in the form of a stick, a lotion, a gel, a spray, and the like. Suitable emulsifiers for the formation of sunscreen emulsions include, for example ethoxylated surfactants known in the art such as Polysorbate-20, Laureth-7, Laureth-4, Sepigel® 305 available from SEPPIC, oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD; and organosilicone emulsifiers such as cetyl dimethicone copolyol-polyglyceryl-4-isostearate-hexylaurate (ABIL® WE 09) available from Goldschmidt Chemical Corporation, behenate dimethicone, cetyl dimethicone copolyol (ABIL® EM 90), (ABIL® EM 97), laurylmethicone copolyol (5200), cyclomethicone and dimethicone copolyol (DC 5225 C and DC 3225 C) available from Momentive Performance Materials Inc., cyclopentasiloxane and dimethicone copolyol, are also available from Momentive Performance Materials, Inc.

Plasticizers may also be added to the sunscreen formulation to improve the flexibility and cosmetic properties of the resulting formulation. Plasticizers are frequently used to avoid brittleness and cracking of film formers, and include, for example, lecithin, polysorbates, dimethicone copolyol, glycols, citrate esters, glycerin, and dimethicone. One skilled in the art may routinely vary the amount of plasticizer desired based on the properties desired and the application envisaged.

The personal care composition of the present invention may optionally contain vitamins or skin nourishing agents, hair nourishing agents, antidandruff additives, antibacterial, and antifungal agents. Some of the preferred agents are ceramides, hyaluronic acid, panthenol, peptides (copper hexapeptide-3), AHAs (lactic acid), retinols (retinyl palmitate)-vitamin A derivatives, vitamin C (1-ascorbic acid), BHAs (salicylic acid), teas (green tea, white tea, red tea), soy and other plant derivatives, isoflavones (grape seed extract), argireline, acai berry, pyridinethione salts, 1-hydroxy-2-pyrrolidone derivatives, 2,2'-dithiobis(pyridine-N-oxide), trihalocarbamides, triclosan, azole compounds such as climbazole, ketoconazole, clotrimazole, econazole, isoconazole and miconazole, selenium sulphides, extracts of one or more non-photosynthetic, non-fruiting filamentous bacteria, zinc pyrithione, piroctone olamine, selenium disulphide, sulphur and coal tar.

The personal care composition of the present invention is preferentially incorporated into a carrier, specifically, a volatile carrier which quickly volatilizes after application. The volatile carriers of the present invention are selected from the group consisting of volatile hydrocarbons, volatile silicones and mixtures thereof. Hydrocarbon oils useful in the present invention include those having boiling points in the range of 60-260° C., more preferably hydrocarbon oils having from about $C_8$ to about $C_{20}$ chain lengths, most preferably $C_8$ to $C_{20}$ isoparaffins. Most preferred are selected from the group consisting of isododecane, isohexadecane, isoeocosane, 2,2,4-trimethylpentane, 2,3-dimethylhexane and mixtures thereof. Preferred volatile silicone fluids include cyclomethicones having 3, 4 and 5 membered ring structures corresponding to the formula $(R_2SiO)_x$, where x is from about 3 to about 6 or linear methicones corresponding to the formula $(R_3SiO(R_2SiO)SiR_3$.

A thickening polymer may be useful in the present invention. The expression "thickening polymer" shall be understood for the purposes of the present invention to mean a polymer having, in solution or in dispersion containing 1% by weight of active material in water or in ethanol at 25° C., a viscosity greater than 0.2 poise at a shear rate of 1 s-I. The viscosity can be measured with a HAAKE RS600 viscometer from THERMO ELECTRON. This viscometer is a controlled-stress viscometer with cone-plate geometry (for example, having a diameter of 60 mm and an angle of 1°). Examples of thickeners include; associative thickeners; crosslinked acrylic acid homopolymers; crosslinked copolymers of (meth)acrylic acid and of $(C_1-C_6)$alkyl acrylate; nonionic homopolymers and copolymers containing ethylenically unsaturated monomers of ester and/or amide type; ammonium acrylate homopolymers or copolymers of ammonium acrylate and of acrylamide; (meth)acrylamido $(C_1-C_4)$alkylsulphonic acid homopolymers and copolymers; crosslinked methacryloyl$(C_1-C_4)$alkyltri$(C_1-C_4)$alkylammonium homopolymers and copolymers. Particulate thickeners may also be used. Also, naturally derived polymers and polymers produced by fermentations may be used such as polysaccharide gums, xanthan gum, pullulan gum, sclerotium gum, carrageenan gum, locust bean gum, alginate, gellan gum, cellulose, carboxymethylcellulose, hydroxyethylcellulose, pectins, starch, chitosan, gelatin and their combination.

Particulates may also be used in combination with the personal care composition of the present invention. Particulates may be organic or inorganic particles. Examples of inorganic particles include microparticles composed of titanium oxide, titanated mica, zirconium oxide, zinc oxide, cerium oxide, magnesium oxide, barium sulfate, calcium sulfate, magnesium sulfate, calcium carbonate, magnesium carbonate, talc, cleaved talc, mica, kaolin, sericite, muscovite, synthetic mica, phlogopite, lepidolite, biotite, lithia mica, silicic acid, silicon dioxide, fumed silica, hydrous silicon dioxide, aluminum silicate, magnesium silicate, aluminum magnesium silicate, calcium silicate, barium silicate, strontium silicate, metal tungstenate salts, hydroxyapatite, vermiculite, higilite, bentonite, montmorillonite, hectorite, zeolite, ceramics, dicalcium phosphate, alumina, aluminum hydroxide, boron nitride, boron nitride or glass, Example of organic particles include powders composed of a polyamide, polyacrylic acid/acrylic acid ester, polyester, polyethylene, polypropylene, polystyrene, styrene/acrylic acid copolymer, divinylbenzene/styrene copolymer, polyurethane, vinyl resin, urea resin, melamine resin, benzoguanamine, polymethylbenzoguanamine, tetrafluoroethylene, polymethylmethacrylate (such as poly(methyl methacrylate)), cellulose, silk, nylon, phenol resin, epoxy resin or polycarbonate.

Useful additives include pH adjusters/buffering agents and chelating agents such as ammonium hydroxide, sodium hydroxide, potassium hydroxide, $C_{12}$-$C_{15}$ alkyl benzoate, citric acid, glycolic acid, lactic acid, sodium citrate, triethanolamine, trolamine, disodium EDTA, edetate disodium, pentasodium pentetate, tetrasodium EDTA, trisodium EDTA.

Fragrance ingredients may be incorporated in the personal care composition of the present invention, e.g., diacetyl, isoamyl acetate, benzaldehyde, cinnamic aldehyde, ethyl propionate, methyl anthranilate, limonene, ethyl decadienoate, allyl hexanoate, ethyl maltol, ethyl vanillin, methyl salicylate, clary extract, eucalyphis globulus oil, grapefruit oil, labdanum oil, masking fragrance, matricaria oil, nopyl acetate, phenoxyethanol, rosewood oil, ylang ylang oil, and perfume oils. There may also be mentioned as perfume oils mixtures of natural and/or synthetic aromatic substances. Natural aromatic substances include, e.g., extracts from blossom (lilies, lavender, roses, jasmine, neroli, ylang-ylang), from stems and leaves (geranium, patchouli, petit-grain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances include, e.g., products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate.

Ethers include, e.g., benzyl ethyl ether; the aldehydes include, e.g., linear alkanals having from 8 to 18 hydrocarbon atoms, citral, citronellal, citronellyl oxyacetaldehyde, cyclamen aldehyde, hydroxycitronellal, lilial and bourgeonal; ketones include, e.g., ionones, isomethylionone and methyl cedryl ketone; alcohols include, e.g., anethol, citronellol, eugenol, isoeugenol, geraniol, linalool, phenyl ethyl alcohol and terpinol; and, hydrocarbons include, e.g., terpenes and balsams.

It is preferable to use mixtures of these and other aromatic substances in combinations that produce an especially attractive scent. Ethereal oils of relatively low volatility, which are chiefly used as aroma components, are also suitable as perfume oils, e.g., sage oil, chamomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α,α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, α-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Flavor ingredients may be used in the personal care composition of the present invention such as stearyl glycyrrhetinate, menthol, cinnamyl alcohol, acetic acid, ascorbic acid, citric acid, fumaric acid, lactic acid malic acid, phosphoric acid, tartaric acid, fruit and plant extracts.

Skin protectants and humectants may be used in the personal care composition of the present invention such as dimethicone, petrolatum, glycerin, ammonium lactate, lanolin, methyl gluceth-20, PEG-20, sorbitol, 1,2,6 hexanetriol, butylene glycol, dipropylene glycol, glycerin, hexylene glycol, panthenol, phytantriol, panthenol, propylene glycol, sodium PCA, sorbitol, triethylene glycol, polyglyceryl sorbitol, glucose, fructose, polydextrose, potassium pca, urea, hydrogenated honey, hyaluronic acid, inositol, hexanediol beeswax, hexanediol beeswax, hydrolyzed elastin, hydrolyzed collagen, hydrolyzed silk, hydrolyzed keratin, erythritol, capryl glycol, and the like.

Hair conditioning agents may be used herein, e.g., hydrocarbons, silicone fluids and cationic materials. Suitable hydrocarbons can be either straight or branched chain and can contain from about 10 to about 16, and preferably from about 12 to about 16, carbon atoms. Examples of suitable hydrocarbons include, e.g., decane, dodecane, tetradecane, tridecane, and mixtures thereof. Examples of suitable silicone fluid conditioning agents include, e.g., linear and cyclic polydimethylsiloxanes, phenyl and alkyl phenyl silicones and silicone copolyols. Cationic conditioning materials agents useful herein include, e.g., quaternary ammonium salts and the salts of fatty amines.

Nail conditioning agents may be incorporated in the present invention, e.g., adipic acid, fumaric acid, tricyclodecane dimethanol copolymer, AMP-isostearoyl hydrolyzed silk, *angelica furcijuga* flower/leaf/stem extract, r-*bacillus licheniformis* keratinase, *bifida/panax ginseng* root cell culture extract ferment filtrate, bis-aminopropyl dimethicone/IPDI copolymer, bis-dicaprolactone ethoxyacrylate IPDI, bis-hEMA IPDI, *boswellia carterii* gum extract, *boswellia serrata* gum extract, calcium hydrolyzed collagen, capryloyl methionine/silk amino acids methyl esters, capryloyl serine/silk amino acid methyl esters, *caulerpa eacemosa* extract, *citrus aurantium amara* (bitter orange) fruit juice extract, *commelina communis* flower/leaf/stem extract, *commiphora myrrha* resin extract, dechloro dihydroxy difluoro ethylcloprostenolamide, deoxyglutamyl fructose, dicaprolactone ethoxyacrylate hema ipdi, dicapryl succinate, dimethyl urea, dipentaerythrityl hexaacrylate, dipentaerythrityl pentaacrylate, *echinacea angustifolia* root extract, *fragaria ananassa* (strawberry) seed oil, fumaric acid/phthalic anhydride/tricyclodecanedimethanol copolymer, *ginkgo biloba* nut extract, glycidoxypropyl trimethoxysilane, honey powder, *hydnocarpus pentandrus* kernel oil, hydrogenated acetophenone/oxymethylene copolymer, hydrolyzed collagen, hydrolyzed keratin, hydrolyzed vinylacetate/vinyl acetoacetate copolymer, *isatis tinctoria* root extract, *kigelia africana* bark extract, leucanthemum vulgare seed extract, leuconostoc/ aloe barbadensis leaf/sorbus aucuparia fruit ferment filtrate, *lobelia inflata* extract, *lupinus texensis* seed extract, *lycium barbarum* fruit extract, *mentha aquatica* extract, methacryloylethyl phosphate, methylene glycol, 2-methylpropanal, *momordica charantia* extract, *narcissus pseudonarcissus* (daffodil) root extract, *opuntia tuna* leaf extract, *opuntia vulgaris* fruit extract, palmitoyl oligopeptide-70, palmitoyl serine/silk amino acids methyl esters, *phaseolus vulgaris* (kidney bean) extract, phlox drummondii seed extract, polyacrylate-12, polyacrylate-30, polyester-18, rosa (american beauty) extract, *rosa borboniana* extract, *rosa roxburghii* seed oil, *rudbeckia hirta* seed extract, silver carp extract, sodium calcium zinc phosphate, *sorbus aucuparia* seed oil, r-spider polypeptide-1, r-spider polypeptide-2, undecenoyl serine/silk amino acid methyl esters, *vaccinium myrtillus* leaf extract, vinyl alcohol/vinylformamide copolymer, *viscum album* (mistletoe) extract, and the like.

Cationic polymers can be used in the personal care composition of the present invention, e.g., cationic guar gum derivatives such as guar hydroxypropyltrimonium chloride and hydroxypropyl guar hydroxypropyltrimonium chloride, available as the Jaguar® series from Rhone-Poulenc.

Ultraviolet light absorbers (UV absorbers) may be useful utilized in the personal care composition herein to protect the composition from chemical or physical deterioration induced by ultraviolet light. UV absorbers, like the sunscreen agents, supra, have the ability to convert incident ultraviolet radiation into less damaging infrared radiation (heat). Suitable UV absorbers include e.g., acetaminosalol, allantoin PABA, benzalphthalide, benzophenones such a benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, and phenone-12, benzotriazolyl dodecyl p-cresol, 3-benzylidene camphor, benzylidenecamphor hydrolyzed collagen sulfonamide, benzylidene camphor sulfonic acid, benzyl salicylate, bis-ethylhexyloxyphenol methoxyphenyl triazine, bornelone, bumetrizole, butyl methoxydibenzoylmethane, butyl PABA, *Callophyllum inophyllum* Seed Oil, *camellia sinensis* leaf extract, carotenoids, ceria/silica, ceria/silica talc, cinoxate, dea-methoxycinnamate, dibenzoxazoyl naphthalene, di-t-butyl hydroxybenzylidene camphor, diethylhexyl butamido triazone, diethylhexyl 2,6-naphthalate, digalloyl trioleate, diisopropyl methyl cinnamate, 1-(3,4-dimethoxyphenyl)-4, 4-dimethyl-1,3-pentanediene, dimethyl PABA ethyl cetearyldimonium tosylate, dimorpholinopyridazinone, diphenyl carbomethoxy acetoxy naphthopyran, disodium bisethylphenyl triaminotriazine stilbenedisulfonate, disodium distyrylbiphenyl disulfonate, disodium phenyl dibenzimidazole tetrasulfonate, drometrizole, drometrizole trisiloxane, esculin, ethyl dihydroxypropyl PABA, ethyl diisopropylcinnamate, ethylhexyl dimethoxybenzylidene dioxoimidazolidine propionate, ethylhexyl dimethyl PABA, ethylhexyl ferulate, ethylhexyl methoxycinnamate, ethylhexyl salicylate, ethylhexyl triazone, ethyl methoxycinnamate, ethyl PABA, ethyl urocanate, etocrylene, ferulic acid, 4-(2-beta-glucopyranosiloxy)propoxy-2-hydroxybenzophenone, glyceryl ethylhexanoate dimethoxycinnamate, glyceryl PABA, glycol salicylate, hexanediol salicylate, homosalate, hydrolyzed lupine protein, isoamyl p-methoxycinnamate, isopentyl trimethoxycinnamate trisiloxane, isopropylbenzyl salicylate, isopropyl dibenzoylmethane, isopropyl methoxycinnamate, menthyl anthranilate, menthyl salicylate, 4-methylbenzylidene camphor, methylene bis-benzotriazolyl tetramethylbutylphenol, octocrylene, octrizole, PABA, PEG-25 PABA, pentyl dimethyl PABA, phenylbenzimidazole sulfonic acid, *pinus pinaster* bark extract, polyacrylamidomethyl benzylidene camphor, polysilicone-15, potassium methoxycinnamate, potassium phenylbenzimidazole sulfonate, Red petrolatum, sodium benzotriazolyl butylphenol sulfonate, sodium isoferulate, sodium phenylbenzimidazole sulfonate, sodium urocanate, *Spirulina platensis* powder, tea-phenylbenzimidazole sulfonate, TEA-salicylate, terephthalylidene dicamphor sulfonic acid, tetrabutyl phenyl hydroxybenzoate, titanium dioxide, tocotrienols, triPABA panthenol, urocanic acid, vinyl acetate/crotonates/methacryloxybenzophenone-1 copolymer and *Vitis vinifera* (grape) seed extract, and polymeric beads or hollow spheres as SPF enhancers. The combination of the UV-absorbers such as those described above with SPF enhancers such as styrene/acrylate copolymers silica beads, spheroidal magnesium silicate, spherical polyamide powder such as n-lactam polymer (Orgasol® range, elf atochem) cross-linked polymethylmethacrylates (pmma; micopearl m305 seppic), may enhance the UV protection. Holosphere additives (Sunspheres® ISP, Silica Shells Kobo.) deflect radiation and the effective path length of the photon is therefore increased. (EP0893119). Some beads, provide a soft feel during spreading. Moreover, the optical activity of such beads, e.g., Micropearl M305, can modulate skin shine by eliminating reflection phenomena and indirectly may scatter UV light.

The personal care composition of the present invention may also contain one or more known and conventional plasticizers in order to improve the flexibility and cosmetic properties of the resulting formulation. Plasticizers are frequently used to avoid brittleness and cracking of film formers and include, e.g., lecithin, polysorbates, dimethicone copolyol, glycols, citrate esters, glycerin, and dimethicone. One skilled in the art may routinely vary the amount of plasticizer(s) depending on the formulation of a particular personal care composition and the properties desired.

The personal care composition of the present invention is preferentially formulated with a carrier, specifically, a volatile carrier which quickly volatilizes after application of the composition. Useful volatile carriers may be selected from the group consisting of volatile hydrocarbons, volatile silicones and mixtures thereof.

Hydrocarbon oils useful in the present invention include those having boiling points in the range of 60-260° C., more preferably hydrocarbon oils having from about $C_8$ to about $C_{20}$ chain lengths, most preferably $C_8$ to $C_{20}$ isoparaffins. Most preferred are isododecane, isohexadecane, isoeocosane, 2,2,4-trimethylpentane, 2,3-dimethylhexane and mixtures thereof.

Volatile silicone fluids include cyclomethicones having 3- to 6-membered ring structures corresponding to the formula $(R_2SiO)_x$, where x is from about 3 to about 6 and linear silicones corresponding to the formula $(R_3SiO(R_2SiO)_xSiR_3$ where x is from about 0 to about 6 and R is a monovalent hydrocarbon radical having from 1 to 6 carbon atoms.

COMPARATIVE EXAMPLES 1-8; EXAMPLES 1-9

The invention is illustrated by, but not limited to, Examples 1 to 9, infra, illustrating the preparation of representative end-functionalized ionic silicones (I) in accordance with the invention and lip color formulations prepared with the ionic silicones (I) of Examples 4-9. Comparative Examples 1-8, infra, illustrating the preparation of silicones outside the scope of the present invention and lip color formulations containing same are presented for comparison purposes only and do not illustrate the invention.

Comparative Example 1

Preparation of Mono-capped Sulfonated Polydimethylsiloxane

A three necked 500 mL flask was charged with 10.0 g (67.5 mmol) of 1,1,1,3,3 pentamethyldisiloxane, 9.5 g (81.0 mmol) alpha-methylstyrene and $1.9 \times 10^{-4}$ g platinum catalyst. The resulting mixture was heated at 115° C. for 48 h while stirring under nitrogen atmosphere. The completion of hydrosilylation was indicated by the disappearance of the silicone hydride peak in the $^1$H NMR. The resulting mixture was vacuum stripped to remove unreacted alphamethylstyrene by placing in an oil bath at 150° C. for 2 h to provide 17.0 g (95%) aryl-substituted disiloxane.

To 5.32 g (20.0 mmol) of the above aryl-substituted siloxane, 4.66 g (40.0 mmol) of chlorosulfonic acid dissolved in 1.0 mL dichlomethane was added drop-wise over a period of 30 minutes while stirring the mixture at ambient temperature. The resulting mixture was continuously stirred for an additional 30 minutes. The completion of the reaction was determined by $^1$H NMR with total sulfonation of the aromatic ring being indicated by the disappearance of the para-substituted aromatic proton peak. The resulting mixture was then vacuum stripped to remove dichloromethane and other volatiles such as chlorosulfonic acid and hydrochloric acid to provide sulfonated cyclotetrasiloxane as a dark brown viscous liquid.

To this sulfonated disiloxane, 118.6 g (400.0 mmol) octamethyltetracyclosiloxane was added with continuous stirring at ambient temperature. After 6 h of reaction, an equilibration of ~82% was indicated by $^{29}$Si NMR. At this point, 12.0 g of triethanol amine were added to the mixture with continuous stirring for an additional 1 h. The resulting mixture was then vacuum stripped overnight to remove volatile cyclic siloxanes such as $D_4$, $D_5$, etc. Finally, 116.0 g of the product was collected as a viscous oil. The polymer had a viscosity of 3.3 Pas at a shear rate of 10 rad/s when measured by a HAAKE Rheometer at 20° C.

Comparative Example 2

Preparation of Sulfobetaine-capped Polydimethylsiloxane

To a three necked 500 mL round-bottom flask were introduced 237.3 g (800.0 mmol) octamethyltetracyclosiloxane, 5.36 g (40.0 mmol) 1,1,3,3 tetramethyldisiloxane and 3.0 g of acidic IER 262 (ion exchange resin). The resulting mixture was continuously stirred 60° C. for 6 h. The reaction mixture was then filtered and vacuum stripped to remove low boiling point silicones resulting in 201.0 g (83%) hydride-terminated polydimethylsiloxane.

A three necked 250 mL flask was charged with 72.0 g (10.0 mmol) of the above hydride-terminated polydimethylsiloxane, 2.5 g (22.0 mmol) allylglycidylether and $1.0 \times 10^{-4}$ g platinum catalyst. The resulting mixture was heated at 70° C. for 24 h with continuous stirring under a nitrogen atmosphere. The complete hydrosilylation of allyglycidylether was indicated by the disappearance of the silicone hydride peak in the $^1$H NMR. The resulting mixture was then vacuum stripped to remove unreacted allylglycidyl ether by placing in an oil bath at 150° C. for 2 h to provide 74.0 g glycidylether-terminated polysiloxane.

To 74.0 g (10.0 mmol) of the above glycidylether-terminated polysiloxane, 2.1 g (20.0 mmol) of diethanol amine and 0.1 g of titanium isopropxide were added consecutively. The resulting mixture was then continuously stirred at 80° C. for 24 h. To this mixture, 2.72 g (20.0 mmol) of butane sultone was added with continuous stirring at 80° C. for an additional 24 h to provide 79 g sulfobetaine-capped polydimethylsiloxane. The polymer had a viscosity of 56.8 Pas at a shear rate of 10 rad/s when measured by a HAAKE Rheometer at 20° C.

Comparative Example 3

Preparation of Trimethylsilyl-capped Polydimethylsiloxane

A three necked 500 mL flask was charged with 0.162 g (1.0 mmol) hexamethydisiloxane, 148.3 g (500.0 mmol) octamethyltetracyclosiloxane and 1.5 g N-catalyst (tetramethylammonium siloxanolate). The reaction mixture was placed in an oil bath with continuous stirring at 80° C. After 8 h of reaction, an equilibration of ~87% was indicated by solid content analysis of the crude reaction mixture. The entire reaction mixture was then vacuum stripped at 150° C. for 2 h to remove volatile cyclic siloxanes. Finally, 130.0 g of trimethylsilyl-capped polydimethylsiloxane was collected as a clear gum. The polymer had a viscosity of 236.2 Pas at a shear rate of 10 rad/s when measured by a HAAKE Rheometer at 20° C.

Comparative Example 4

Preparation of Pendant Sodium Sulfonate-functional Polyorganosiloxane

To the sulfonic acid-functional cyclotetrasiloxane 5.7 g (8.0 mmol) obtained in Example 2, infra, 474.7 g (1600.0 mmol) octamethyltetracyclosiloxane and 2.96 g (16.0 mmol) 1,1,3,3-tetramethyl-1,3-divinyldisiloxane were added with continuous stirring at ambient temperature. After reaching equilibrium of ~87 wt % of the linear siloxanes, the reaction mixture was neutralized using 10.0 g (128.0 mmol) moistened sodium bicarbonate at 70° C. Vacuum stripping of the reaction mixture at low pressure resulted in 411.0 g of product in the form of a milky oil. NMR analysis of the product indicated that the polymer was a pendant-sulfonated polydimethylsiloxane. The polymer had a viscosity of 5.0 Pas at a shear rate of 10 rad/s when measured by a HAAKE Rheometer at 20° C.

Comparative Example 5

Preparation of Pendant Sodium Sulfonate-functional Polyorganosiloxane

To the sulfonic acid-functional cyclotetrasiloxane 5.7 g (8.0 mmol) obtained in Example 2, infra, 474.7 g (1600.0 mmol) octamethyltetracyclosiloxane and 14.8 g (80.0 mmol) 1,1,3,3-tetramethyl-1,3-divinyldisiloxane were added with continuous stirring at ambient temperature. After reaching equilibrium of ~87 wt % of the linear siloxanes, the reaction mixture was neutralized using 10.0 g (128.0 mmol) moistened sodium bicarbonate at 70° C. The vacuum stripping of the reaction mixture at low pressure resulted in 427.0 g of product as a viscous gum. NMR analysis of the product indicated that the polymer was a pendant-sulfonated polydimethylsiloxane.

Comparative Example 6

Preparation of Sodium Carboxylate-functional Polyorganosiloxane

A 1000 ml three necked round bottom flask equipped with a condenser was charged with 184.28 g (1M) undecenoic acid and 300 ml toluene. The solution was heated to 70° C. and 80.7 g (0.5M) hexamethyldisilazane added thereto over a period of 2 h. The solution was continuously stirred at 70-80° C. for 4 h. The solution was stripped of solvent, the reaction mass being distilled under vacuum at 1-5 Hg pressure and 150-160° C. to provide undecenoic acid trimethylsilylester (A). A 1000 ml three necked round bottom flask equipped with a condenser was charged with 1.34 g (0.01M) tetramethyldisiloxane, 296.6 g (1M) octamethylcyclotetrasiloxane and 6 g acidic ion exchange resin. The solution was continuously stirred for 12 h at 55-60° C. to provide hydride-terminated siloxane (B).

A 1000 ml three necked round bottom flask equipped with a condenser was charged with 5.1 g (0.016 M) of above compound (A), 237.8 g (0.008M) of above compound (B) and 0.0003 g Platinum Karstedt's catalyst with the solution being continuously stirred for 8 h at 90° C. Subsequent deprotection and neutralization with sodium bicarbonate resulted in product sodium carboxylate-functional polydimethylsiloxane. The polymer had a viscosity of 18 Pas at a shear rate of 10 rad/s when measured by a HAAKE Rheometer at 20° C.

Comparative Example 7

Preparation of Sodium Phosphate-functional Polyorganosiloxane

A 1000 ml three necked round bottom flask equipped with a condenser was charged with 256.3 g (2 M) allylglycidylether and 0.0003 g platinum Karstedt's catalyst and the solution was heated to 70° C. To this solution, 134.3 g (1M) tetramethyldisiloxane was added drop-wise over a period of 6 h at 70-75° C. accompanied by further stirring for 6 h at 90° C. to provide epoxy-functional tetramethyldisiloxane.

A 1000 ml three necked round bottom flask equipped with a condenser was charged with 3.9 g (0.03M) of the above product, 296.6 g (1M) octamethyldisiloxane and 6 g acidic ion exchange resin with the solution being continuously stirred for 16 h at 70° C. to result in epoxy-functional polydimethylsiloxane.

A 1000 ml three necked round bottom flask equipped with a condenser was charged with 150 g (0.005M) of the above product and 1.2 g (0.01M) phosphoric acid (85%) with the solution being continuously stirred at 85-90° C. for 4 h. The solution was then cooled to about 15° C. and 0.8 g (0.02M) sodium hydroxide solution dissolved in 1 ml water added thereto accompanied by stirring at 15-20° C. for 2 h to provide sodium phosphate-functional polydimethylsiloxane. NMR analysis of the product indicated that the polymer was a phosphate-functionalized polyorganosiloxane.

Comparative Example 8

Preparation of Sodium Carboxylate-functional Polyorganosiloxane

A 1000 ml three necked round bottom flask equipped with a condenser was charged with 184.28 g (1M) undecenoic acid and 300 ml toluene. The solution was heated to 70° C. which was then added 80.7 g (0.5M) hexamethyldisilazane over the period of 2 h. The solution was continuously stirred at 70-80° C. for 4 h. The solution was stripped of solvent and low boiling reagent with the reaction mass being distilled under 1-5 mm Hg vacuum and 150-160° C. to provide undecenoic acid trimethylsilylester (A).

A 1000 ml three necked round bottom flask equipped with a condenser was charged with 6.7 g (0.05M) tetramethyldisiloxane, 185.4 g (0.625M) octamethylcyclotetrasiloxane and 5 g acidic ion exchange resin. The solution was continuously stirred for 12 h at 55-60° C. to result in hydride-terminated siloxane (B).

A 1000 ml three necked round bottom flask equipped with a condenser was charged with 10.3 g (0.04 M) of the above compound (A), 76.4 g (0.02 M) of the above compound (B) and 0.0001 g Platinum Karstedt's catalyst with the solution continuously stirred for 8 h at 90° C. Subsequent deprotection and neutralization with sodium bicarbonate resulted in sodium carboxylate-functional polydimethylsiloxane. The polymer had a viscosity of 283 Pas at a shear rate of 10 rad/s when measured by a HAAKE Rheometer at 20° C.

Example 1

Preparation of Sulfonic Acid-functional Tetramethyldisiloxane

A three necked 500 mL flask was charged with 18.16 g (154.0 mmol) alpha-methylstyrene and $27.2 \times 10^{-5}$ g platinum catalyst. The temperature of the resulting mixture was brought to 115° C., after which 9.40 g (70.0 mmol) 1,1,3,3 tetramethyldisiloxane was added drop-wise under continuous stirring until completion of the hydrosilylation reaction. Completion of hydrosilylation was indicated by the disappearance of the silicone hydride peak in the $^1$H NMR. The resulting mixture was vacuum stripped to remove unreacted alpha-methylstyrene by placing in an oil bath at 150° C. for 2 h whereby 23.2 g aralkylene-substituted disiloxane was obtained. (Yield: 90%)

To this aralkylene-substituted disiloxane (23.2 g, 62.4 mmol) were added 29.6 g (252.8 mmol) of chlorosulfonic acid drop-wise over a period of 30 minutes with the mixture being continuously stirred at ambient temperature. Stirring was continued for an additional 30 minutes. Completion of the reaction was determined by $^1$H NMR with total sulfonation of the aromatic ring being indicated by the disappearance of the para-substituted aromatic proton peak. Vacuum stripping of the reaction mixture at low pressure resulted in 33.0 g of sulfonated disiloxane as a brown viscous oil.

Example 2

Preparation of Sulfonic Acid-functional Tetramethyltetracyclosiloxane

A three necked 500 mL flask was charged with 70.08 g (60.0 mmol) alpha-methylstyrene and $10.0 \times 10^{-4}$ g platinum catalyst. The temperature of the resulting mixture was brought to 115° C., after which 30.0 g (120.5 mmol) of 1,3,5,7-tetramethylcyclotetrasiloxane was added drop-wise under continuous stirring. The progress of the reaction was monitored by $^1$H NMR. After 12 h of reaction, complete conversion of silicone hydride was indicated by the $^1$H NMR. The reaction mixture was then vacuum stripped at 150° C. for 2 h to remove unreacted alpha-methylstyrene and provide 80.5 g of aralkylene-substituted cyclotetrasiloxane. (Yield: 95%)

To 14.24 g (20.0 mmol) of the above aralkylene-substituted cyclotetrasiloxane was added 18.64 g (160.0 mmol) chlorosulfonic acid dissolved in 4.0 mL dichloromethane drop-wise over a period of 30 minutes with the mixture being continuously stirred at ambient temperature. The resulting mixture was stirred for an additional 30 minutes. Completion of the reaction was indicated by $^1$H NMR with complete sulfonation of the aromatic ring being indicated by the disappearance of the para-substituted aromatic proton peak. Vacuum stripping of the reaction mixture at low pressure resulted in 20.6 g of the sulfonic acid-functional cyclotetrasiloxane as a brown viscous gum.

Example 3

Preparation of Sodium Sulfonate-capped Polydimethylsiloxane

A three necked 500 mL flask was charged with 42.4 g (80.0 mmol) sulfonated disiloxane from Example 1, supra, and 118.0 g (400.0 mmol) of octamethyltetracyclosiloxane. The reaction mixture was placed in an oil bath with continuous stirring at ambient temperature. After reaching an equilibrium of ~87 wt % of the linear siloxanes, the reaction mixture was neutralized using 26.88 g (320.0 mmol) of moistened sodium bicarbonate at 70° C. The vacuum stripping of the reaction mixture at low pressure gave the expected product as a white solid. NMR analysis of the product indicated that the polymer was a sulfonated-capped polydimethylsiloxane.

Example 4

Preparation of Sodium Sulfonate-capped Polydimethylsiloxane

A three necked 500 mL flask was charged with 21.2 g (40.0 mmol) sulfonated disiloxane from Example 1, supra, and 118.0 g (400.0 mmol) octamethyltetracyclosiloxane. The reaction mixture was placed in an oil bath with continuous stirring at ambient temperature. After reaching an equilibrium of ~87 wt % of the linear siloxanes, the reaction mixture was neutralized using 13.44 g (160.0 mmol) of moistened sodium bicarbonate at 70° C. The vacuum stripping of the reaction mixture at low pressure resulted in 123.4 g of the product as a viscous gum. NMR analysis of the product indicated that the polymer was a sulfonated-capped polydimethylsiloxane. The polymer had a viscosity of 1325 Pas at a shear rate of 10 rad/s when measured by a HAAKE Rheometer at 20° C.

Example 5

Preparation of Sodium Sulfonate-capped Polydimethylsiloxane

A three necked 500 mL flask was charged with 10.6 g (20.0 mmol) sulfonated disiloxane from Example 1, supra, and 118.0 g (400.0 mmol) octamethyltetracyclosiloxane.

The reaction mixture was placed in an oil bath with continuous stirring at ambient temperature. After reaching an equilibrium of ~87 wt % of the linear siloxanes, the reaction mixture was neutralized using 6.7 g (80.0 mmol) of moistened sodium bicarbonate at 70° C. The vacuum stripping of the reaction mixture at low pressure resulted in 112.0 g of the product a viscous gum. NMR analysis of the product indicated that the polymer was a sulfonated-capped polydimethylsiloxane. The polymer had a viscosity of 1230 Pas at a shear rate of 10 rad/s when measured by a HAAKE Rheometer at 20° C.

Example 6

Preparation of Sodium Sulfonate-capped Polydimethylsiloxane

A three necked 250 mL flask was charged with 2.12 g (4.0 mmol) sulfonated disiloxane from Example 1, supra, and 59.3 g (200.0 mmol) octamethyltetracyclosiloxane. The reaction mixture was placed in an oil bath and continuously stirred at ambient temperature. After reaching an equilibrium of ~87 wt % of the linear siloxanes, the reaction mixture was neutralized using 1.4 g (16.0 mmol) of moistened sodium bicarbonate at 70° C. The vacuum stripping of the reaction mixture at low pressure yielded 53.0 g of product as a viscous gum. NMR analysis of the product indicated that the polymer was a sulfonated-capped polydimethylsiloxane. The polymer had a viscosity of 100 Pas at a shear rate of 10 rad/s when measured by a HAAKE Rheometer at 20° C.

Example 7

Preparation of Sodium Sulfonate-capped Polydimethylsiloxane

A three necked 250 mL flask was charged with 1.1 g (2.0 mmol) sulfonated disiloxane from Example 1, supra, and 59.3 g (200.0 mmol) octamethyltetracyclosiloxane. After reaching an equilibrium of ~87 wt % of the linear siloxanes, the reaction mixture was neutralized using 0.7 g (8.0 mmol) of moistened sodium bicarbonate at 70° C. Vacuum stripping of the reaction mixture at low pressure yielded 49.0 g of product as a viscous gum. NMR analysis of the product indicated that the polymer was a sulfonated-capped polydimethylsiloxane. The polymer had a viscosity of 53 Pas at a shear rate of 10 rad/s when measured by a HAAKE Rheometer at 20° C.

Similarly, calcium, mMagnesium, zinc, silver and cobalt salts of sulfonate-capped polydimethylsiloxanes (PDMS) were been synthesized via neutralization of the sulfonic acid-capped podimethylsiloxane with the respective oxide.

Example 8

Preparation of Sodium Sulfonate-capped Polydimethylsiloxane

A three necked 250 mL flask was charged with 0.55 g (1.0 mmol) sulfonated disiloxane from Example, supra, and 148.3 g (500.0 mmol) octamethyltetracyclosiloxane. After reaching an equilibrium of ~87 wt % of the linear siloxanes, the reaction mixture was neutralized using 0.4 g (4.0 mmol) of moistened sodium bicarbonate at 70° C. Vacuum stripping of the reaction mixture at low pressure resulted in 132.0 g of product as a viscous gum. NMR analysis of the product indicated that the polymer was a sulfonated-capped polydimethylsiloxane. The polymer had a viscosity of 1209 Pas at a shear rate of 10 rad/s when measured by a HAAKE Rheometer at 20° C.

Example 9

Preparation of Triethanolammonium Sulfonate-capped Polydimethylsiloxane

A three necked 500 mL flask was charged with 10.6 g (20.0 mmol) sulfonic acid functional disiloxane from Example 1, supra, and 118.0 g (400.0 mmol) of octamethyltetracyclosiloxane. The reaction mixture was placed in an oil bath with continuous stirring at ambient temperature. After reaching an equilibrium of ~87 wt % of the linear siloxanes, the reaction mixture was neutralized using 8.56 g (80.0 mmol) of triethanolamine at 70° C. Vacuum stripping of the reaction mixture at low pressure gave 114.0 g of product as a viscous gum. The polymer had a viscosity of 5399 Pas at a shear rate of 10 rad/s when measured by a HAAKE Rheometer at 20° C.

For purposes of comparison, lip color formulations (LCFs) were prepared incorporating non-functionalized the silicones and the silicones of Comparative Examples 1-8 (LCFs 1-15) and compared with LCFs incorporating end-functionalized ionic silicones (I) of Examples 4-9 (LCFs 16-26). The LCFs were evaluated for their performance characteristics (Transfer Resistance, Water Resistance, Tackiness, Gloss and Trans Epidermal Water Loss) as hereinbelow described.

TABLE 1A

Lip Color Formulations (LCFs) 1 and 2 (Control: No Functionalized or Ionic Silicone) and LCFs 3-15 (Silicones of Comparative Examples 1-8)

| Comparative Example, Amount (g) | LCF 1 | LCF 2 | LCF 3 | LCF 4 | LCF 5 | LCF 6 | LCF 7 | LCF 8 | LCF 9 | LCF 10 | LCF 11 | LCF 12 | LCF 13 | LCF 14 | LCF 15 |
|---|---|---|---|---|---|---|---|---|---|---|---|---|---|---|---|
| Silicone of Comp. Ex. 1 | — | — | — | — | — | 2.5 | — | — | — | — | — | — | — | — | — |
| Silicone of Comp. Ex. 2 | — | — | — | — | 2.5 | — | — | — | — | — | — | — | — | — | — |
| Silicone of Comp. Ex. 3 | — | — | 2.5 | 1 | — | — | — | — | — | — | — | — | — | — | — |
| Silicone of Comp. Ex. 4 | — | — | — | — | — | — | 2.5 | 1 | — | — | — | — | — | — | — |
| Silicone of Comp. Ex. 5 | — | — | — | — | — | — | — | — | 2.5 | 1 | — | — | — | — | — |

TABLE 1A-continued

Lip Color Formulations (LCFs) 1 and 2 (Control: No Functionalized or Ionic Silicone) and LCFs 3-15 (Silicones of Comparative Examples 1-8)

| Comparative Example, Amount (g) | LCF 1 | LCF 2 | LCF 3 | LCF 4 | LCF 5 | LCF 6 | LCF 7 | LCF 8 | LCF 9 | LCF 10 | LCF 11 | LCF 12 | LCF 13 | LCF 14 | LCF 15 |
|---|---|---|---|---|---|---|---|---|---|---|---|---|---|---|---|
| Silicone of Comp. Ex. 6 | — | — | — | — | — | — | — | — | — | — | 2.5 | 1.0 | — | — | — |
| Silicone of Comp. Ex. 7 | — | — | — | — | — | — | — | — | — | — | — | — | 2.5 | 1.0 | — |
| Silicone of Comp. Ex. 8 | — | — | — | — | — | — | — | — | — | — | | | | | 2.5 |

TABLE 1B

Remaining Components of LCFs 1-15

| Remaining Other Components, Amount (g) | LCF 1 | LCF 2 | LCF 3 | LCF 4 | LCF 5 | LCF 6 | LCF 7 | LCF 8 | LCF 9 | LCF 10 | LCF 11 | LCF 12 | LCF 13 | LCF 14 | LCF 15 |
|---|---|---|---|---|---|---|---|---|---|---|---|---|---|---|---|
| SE30 (PDMS Gum), Momentive Performance Materials | 2.5 | 1 | — | — | — | — | — | — | — | — | — | — | — | — | — |
| SR1000 (Silicone Resin), Momentive Performance Materials | — | 1.5 | — | 1.5 | — | — | — | 1.5 | — | 1.5 | — | 1.5 | — | 1.5 | — |
| Bentone Gel VS-5 PC V (Thickener), Elementis Specialties Inc. | 0.81 | 0.81 | 0.81 | 0.81 | 0.81 | 0.81 | 0.81 | 0.81 | 0.81 | 0.81 | 0.81 | 0.81 | 0.81 | 0.81 | 0.81 |
| IDD (Solvent), Presperse LLC | 4 | 4 | 4 | 4 | 4 | 4 | — | — | — | — | — | — | — | — | — |
| D5 (Solvent), Momentive Performance Materials | — | — | — | — | — | — | 4 | 4 | 4 | 4 | 4 | 4 | 4 | 4 | 4 |
| Red Shade Dispersion "GE" (Pigment), International Foodcraft Corp. | 2.4 | 2.4 | 2.4 | 2.4 | 2.4 | 2.4 | 2.4 | 2.4 | 2.4 | 2.4 | 2.4 | 2.4 | 2.4 | 2.4 | 2.4 |
| TiO2-MT100 TV (Pigment), Tri-K Industries | 0.29 | 0.29 | 0.29 | 0.29 | 0.29 | 0.29 | 0.29 | 0.29 | 0.29 | 0.29 | 0.29 | 0.29 | 0.29 | 0.29 | 0.29 |
| DI Water | — | — | — | — | 1.24 | 1.24 | — | — | — | — | 1.24 | 1.24 | 1.24 | 1.24 | 1.24 |
| Glycerin (Moisturizer) m Sigma-Aldrich Inc. | — | — | — | — | — | — | 1.24 | 1.24 | 1.24 | 1.24 | — | — | — | — | — |

TABLE 2A

LCFs 16-26 Ionic Silicones of Examples 4-9

| Example, Amount (g) | LCF 16 | LCF 17 | LCF 18 | LCF 19 | LCF 20 | LCF 21 | LCF 22 | LCF 23 | LCF 24 | LCF 25 | LCF 26 |
|---|---|---|---|---|---|---|---|---|---|---|---|
| Ionic Silicone (I) of Ex. 4 | 2.50 | 1.00 | | | | | | | | | |
| Ionic Silicone (I) of Ex. 5 | | | 1.00 | | | | | | 2.50 | 1 | |

TABLE 2A-continued

LCFs 16-26 Ionic Silicones of Examples 4-9

| Example, Amount (g) | LCF 16 | LCF 17 | LCF 18 | LCF 19 | LCF 20 | LCF 21 | LCF 22 | LCF 23 | LCF 24 | LCF 25 | LCF 26 |
|---|---|---|---|---|---|---|---|---|---|---|---|
| Ionic Silicone (I) of Ex. 6 | | | | 1.00 | | | | | | | |
| Ionic Silicone (I) of Ex. 7 | | | | | 1.00 | | | | | 2.50 | 1 |
| Ionic Silicone (I) of Ex. 8 | | | | | | 1.00 | | | | | |
| Ionic Silicone (I) of Ex. 9 | | | | | | | 2.50 | | | | |

TABLE 2B

Remaining Components of LCFs 16-26

| Remaining Components, (g) | LCF 16 | LCF 17 | LCF 18 | LCF 19 | LCF 20 | LCF 21 | LCF 22 | LCF 23 | LCF 24 | LCF 25 | LCF 26 |
|---|---|---|---|---|---|---|---|---|---|---|---|
| SR1000 (Silicone Resin), Momentive Performance Materials | | 1.50 | 1.50 | 1.50 | 1.5 | 1.5 | | — | 1.5 | — | 1.5 |
| Bentone Gel VS-5 PC V (Thickener), Elementis Specialties Inc. | 0.81 | 0.81 | 0.81 | 0.81 | 0.8 | 0.8 | 0.8 | 0.81 | 0.81 | 0.81 | 0.81 |
| IDD (Solvent), Presperse LLC | 4.00 | 4.00 | 4.00 | 4.00 | 4 | 4 | 4 | — | — | — | — |
| D5 (Solvent), Momentive Performance Materials | | | | | | | | 4.00 | 4 | 4 | 4 |
| Red Shade Dispersion, "GE" (Pigment), International Foodcraft Corp. | 2.40 | 2.40 | 2.40 | 2.40 | 2.4 | 2.4 | 2.4 | 2.40 | 2.4 | 2.4 | 2.4 |
| TiO2- MT100 TV (Pigment), Tri-K Industries | 0.29 | 0.29 | 0.29 | 0.29 | 0.3 | 0.3 | 0.3 | 0.29 | 0.29 | 0.29 | 0.29 |
| DI Water | 1.24 | 1.24 | | | | 1.24 | | | | | |
| Glycerin (Moisturizer), Sigma-Aldrich Inc. | | | | | | | | 1.24 | 1.24 | 1.24 | 1.24 |

A. Transfer Resistance Properties.

The transfer resistance properties of LCFs 1-26 were measured using the method described in U.S. Pat. No. 6,074,654 with the following exceptions:

Each LCF was individually applied to an artificial skin film (pre-hydrated over 30% aqueous glycerin solution for 24 h) and dried at 40° C. The films were then subjected to a rubbing "insult" using a tester device. A 500 g mass was covered with a piece of white cotton knit cloth. The assembly was placed on the surface of the coated in vitro skin. The assembly was rotated 360°. The cloth was then electronically imaged and the percent area darkened by the transferred LCF was determined by image processing software. The higher the % transfer, the more LCF transferred from the coated in vitro skin to the white cloth. This process was repeated on the same location of each in vitro skin. Each rotation (360°) of the abrasive surface across the dried film was counted as one insult. The maximum transfer coverage is considered to be 100%, which means that the entire abrasive surface is covered by LCF material. Lower % transfer is indicative of better transfer resistance. The results of the transfer resistance testing are set forth in Tables 3 and 4 as follows:

TABLE 3

Transfer Resistance of LCFs 1 and 2 (No Functionalized or Ionic Silicone) and LCFs 3-15 (Silicones of Comparative Examples 1-8)

| | LCF 1 | LCF 2 | LCF 3 | LCF 4 | LCF 5 | LCF 6 | LCF 7 | LCF 8 | LCF 9 | LCF 10 | LCF 11 | LCF 12 | LCF 13 | LCF 14 | LCF 15 |
|---|---|---|---|---|---|---|---|---|---|---|---|---|---|---|---|
| Insult 1 | 91% | 19% | 89% | 45% | 54% | 76% | 67% | 48% | 61% | 16% | 56% | 34% | 67% | 39% | 30% |
| Insult 2 | 92% | 4% | 90% | 59% | 28% | 76% | 24% | 29% | 19% | 13% | 17% | 11% | 18% | 21% | 4% |
| Insult 3 | 83% | 2% | 87% | 27% | 17% | 74% | 7% | 9% | 5% | 14% | 7% | 5% | 8% | 9% | 3% |
| Insult 4 | 85% | 1% | 78% | 4% | 10% | 73% | 3% | 10% | 2% | 4% | 9% | 4% | 3% | 9% | 2% |
| Insult 5 | 59% | 0% | 8% | 4% | 12% | 72% | 3% | 11% | 1% | 3% | 3% | 6% | 3% | 7% | 0% |

TABLE 4

Transfer Resistance Properties of LCFs 16-26 (Ionic Silicones (I) of Examples 4-9)

| | LCF 16 | LCF 17 | LCF 18 | LCF 19 | LCF 20 | LCF 21 | LCF 22 | LCF 23 | LCF 24 | LCF 25 | LCF 26 |
|---|---|---|---|---|---|---|---|---|---|---|---|
| Insult 1 | 1% | 0% | 0% | 0% | 1% | 35% | 37% | 36% | 9% | 58% | 4% |
| Insult 2 | 1% | 0% | 0% | 0% | 0% | 2% | 36% | 13% | 7% | 23% | 4% |

TABLE 4-continued

Transfer Resistance Properties of LCFs 16-26 (Ionic Silicones (I) of Examples 4-9)

|  | LCF 16 | LCF 17 | LCF 18 | LCF 19 | LCF 20 | LCF 21 | LCF 22 | LCF 23 | LCF 24 | LCF 25 | LCF 26 |
|---|---|---|---|---|---|---|---|---|---|---|---|
| Insult 3 | 0% | 0% | 0% | 0% | 1% | 2% | 13% | 7% | 9% | 13% | 5% |
| Insult 4 | 1% | 0% | 0% | 0% | 0% | 1% | 10% | 2% | 3% | 4% | 4% |
| Insult 5 | 0% | 0% | 0% | 0% | 0% | 2% | 13% | 2% | 1% | 3% | 4% |

B. Water Resistance Properties

The water resistance properties of LCFs 1 and 2 (no functionalized or ionic silicone) and LCFs 17-20 (ionic silicones (I) of Examples 4-7) were determined. The in vitro skin was prepared in the same manner as described above. Once the LCF coating was dried on the surface of the skin, a thin layer of water was applied thereto and allowed to remain for 15 minutes. After excess water was shaken off, the transfer test was performed. The results of the water resistance testing are set forth in Table 5 as follows:

TABLE 5

Water Resistance Properties

| Water Resistance | LCF 1 | LCF 2 | LCF 17 | LCF 18 | LCF 19 | LCF 20 |
|---|---|---|---|---|---|---|
| Insult 1 | 19% | 93% | 0% | 0% | 1% | 1% |

C. Tackiness

The tackiness properties of LCF 2 (no functionalized or ionic silicone) and LCFs 20 and 23-25 (ionic silicones (I) of Examples 5 and 7, respectively) were determined. The in vitro skin was prepared in the same manner as described above. Once an LCF had dried on the in vitro skin, the tack force of the dried film was measured using a Dia-Stron (MTT 175) instrument, the lower the tack-force, the lesser the tackiness of the LCF. The results of the tackiness testing are set forth in Table 6 as follows:

TABLE 6

Tackiness Properties

| Tack Force (gmt) | LCF 2 | LCF 20 | LCF 23 | LCF 24 | LCF 25 |
|---|---|---|---|---|---|
| Reading 1 | 49.7 | 4.9 | 0.4 | 3.55 | 46.4 |
| Reading 2 | 51.85 | 4.85 | 0.6 | 4.75 | 33.7 |
| Reading 3 | 52.15 | 4.55 | 0.55 | 5.65 | 31.95 |
| Reading 4 | 52.65 | 4.8 | 0.75 | 6.25 | 30.35 |
| Reading 5 | 54.05 | 4.95 | 0.95 | 6.3 | 29.4 |
| Average | 52.08 +/−1.57 | 4.81 +/−0.15 | 0.65 +/−0.21 | 5.3 +/−1.16 | 34.36 +/−6.92 |

D. Gloss Properties

The gloss properties of LCF 2 (no functionalized or ionic silicone) and LCFs 24 and 26 (ionic silicones (I) of Examples 5 and 17, respectively) were determined. A film of uniform thickness of each formulation was made on a standard leneta card and dried at 40° C. The 60° and 85° gloss readings of the dried films were recorded using a BYK glossmeter. The results of the gloss testing are set forth in Table 7 as follows:

| Gloss, degrees | LCF 2 | LCF 23 | LCF 24 | LCF 26 |
|---|---|---|---|---|
| 60° | 18.5 | 52.8 | 20.5 | 36.2 |
| 85° | 66.3 | 78.4 | 72.1 | 78.4 |

E. Trans Epidermal Water Loss (TEWL) Properties

The transepidermal water loss (TEWL) properties of an uncoated in vitro skin and those coated with LCF 2 (no functionalized or ionic silicone), LCFs 8 and 9 (silicones of Comparative Examples 4 and 5, respectively) and LCFs 23 and 26 (end-functionalized ionic silicones of Examples 5 and 7, respectively) of the present invention were measured using the method describe in U.S. Pat. No. 5,679,335 with the following exceptions:

The hydrated in vitro skin was coated with the indicated LCF and dried at 40° C. overnight. A set of Pyne cups was charged with 3.00 ml of water and covered with dried in vitro skin coated with the individual LCF. The rate of water loss from the skin surface was measured using a Tewameter® TM 300 probe attached to an MPA 580 instrument. The results of the TWEL testing are set forth in Table 8 as follows:

TABLE 8

TEWL Properties

|  | Uncoated | LCF 2 | LCF 8 | LCF 9 | LCF 23 | LCF 26 |
|---|---|---|---|---|---|---|
| TEWL (g/mh$^2$) | 10.5 | 7.70 | 9.9 | 9.8 | 8.7 | 6.9 |

As the data in Tables 3-8, supra, show, personal care compositions incorporating end-functionalized ionic silicones (I) in accordance with this invention exhibit improved product performance characteristics compared with personal care compositions incorporating non-functionalized silicones or ionic silicones outside the scope of this invention. Thus, e.g., in the case of lip color formulations containing end-functionalized silicones (I) of the invention, the formulations exhibited significant improvement in their transfer resistance, water resistance, gloss, reduction in tackiness and trans epidermal water loss properties compared with other silicones.

Hair care formulations (HCFs) were prepared with an ionic silicone in accordance with the invention (HCF1 containing the end-functionalized ionic silicone of Example 5), a nonfunctionalized silicone (HCF2), and silicones outside the scope of the invention (HCF3 and HCF4 containing silicones of Comparative Examples 1 and 2) and evaluated for their gloss, softness and antifrizz properties. The composition of HCFs 1-4 is set forth in Table 9 as follows:

TABLE 9

Hair Care Formulations (HCFs) 1-4

| | HCF Components, Amount (g) | HCF 1 | HCF 2 | HCF 3 | HCF 4 |
|---|---|---|---|---|---|
| Phase A | Deionized water | 93.7 | 93.7 | 93.7 | 93.7 |
| | 2-hydroxyethylcellulose (Thickener), Aldrich Chemical Company Inc. | 1.2 | 1.2 | 1.2 | 1.2 |
| | Glycerine (Thickener) Merck Inc. | 2.0 | 2.0 | 2.0 | 2.0 |
| Phase B | Ionic Silicone of Example 5 | 0.5 | — | — | — |
| | SE30 (PDMS Gum), Momentive Performance Materials | — | 0.5 | — | — |
| | Silicone of Comparative Example 1 | — | — | 0.5 | — |
| | Silicone of Comparative Example 2 | — | — | — | 0.5 |
| | TMN-6 (Emulsifier), Sigma-Aldrich Inc. | 0.1 | 0.1 | 0.1 | 0.1 |
| | TMN-10 (Emulsifier), Sigma-Aldrich Inc. | 0.2 | 0.2 | 0.2 | 0.2 |
| | IDD (Solvent), Presperse LLC | 0.5 | 0.5 | 0.5 | 0.5 |
| | Deionized water | 1.8 | 1.8 | 1.8 | 1.8 |

The physical properties of HCFs 1-4 are set forth in Table 10 as follows:

TABLE 10

Physical Properties of HCFs 1-4

| | HCF1 | HCF2 | HCF3 | HCF4 |
|---|---|---|---|---|
| Viscosity (Pa-s) | 3.41 | 3.34 | 5.90 | 3.51 |
| Stability (5 days Room Temperature) | Yes | Yes | Yes | Yes |
| Stability (5 days at 50° C.) | Yes | No | Yes | Yes |

A. Gloss and Softness Properties of HCFs 1-4 on Hair

About 2 g of each HCF was applied on a hair tress (~2.0 g) in such a manner that most or all of the hair fiber was contacted with the composition. Then, the hair tresses were rinsed out with water and dried with a hair-dryer. The gloss of a dried hair tress was then measured using a BYK-Gardner glossmeter at three different angles (results set forth in Table 11). The "softness" feel of the treated hair tresses was evaluated based on pair-wise comparisons between two traces by five panelists (results set forth in Table 12).

TABLE 11

Gloss Results

| | HCF1 | HCF4 | HCF2 | HCF3 |
|---|---|---|---|---|
| Gloss at 20° (GU) | 0.7 | 0.7 | 0.6 | 0.7 |
| Gloss at 60° (GU) | 3.5 | 3.2 | 3.2 | 3.3 |
| Gloss at 85° (GU) | 1.6 | 1.1 | 1.1 | 1.2 |

TABLE 12

Panel Pair Comparison Results for Softness Evaluation

| Pair | Results |
|---|---|
| HCF1/HCF2 | 80% considered HFC1 better than HCF2 |
| HCF1/HCF3 | 60% considered HFC1 better than HCF3 |
| HCF1/HCF4 | 60% considered HFC1 better than HCF4 |
| HCF2/HCF3 | 60% considered HCF3 better than HCF2 |
| HCF2/HCF4 | 60% considered HCF4 better than HCF2 |
| HCF3/HCF4 | 60% considered HCF4 better than HCF3 |

These results indicate that the sulfonate-capped silicone-based formulation (HFC1) of the invention improved the hair conditioning with respect to both gloss and softness feel compared to the comparative and commercial benchmark (HFCs 2-4).

Sprayable conditioner formulations (SCFs) were prepared as set forth in Table 13 below:

TABLE 13

Sprayable Conditioner Formulation of End-sulfonated and Comparative Silicones

| SCF Components, Amount (g) | SCF1 | SCF2 | SCF3 | SCF4 |
|---|---|---|---|---|
| SE30 (PDMS Gum), Momentive Performance Materials | 0.9 | — | — | — |
| SR1000 (Silicone Resin), Momentive Performance Materials | 0.6 | — | — | — |
| Ionic Silicone of Example 5 | — | 1.6 | — | — |
| Silicone of Comparative Example 1 | — | — | 1.6 | — |
| IDD (Solvent), Presperse LLC | 25.0 | 25.0 | 25.0 | 25.0 |
| Water | — | 1 | — | — |

B. Anti-Frizz Properties

Each SCF was sprayed onto 2.0 of platinum beached hair tress using a spraying bottle (total six sprays in each tress) and massaged it well on hair as to confirmed uniform application of the formulation. The tresses were then dried using an automated air dryer. After, complete drying, the samples were placed vertically into the humidity chamber (25° C., 90% RH) for 1 h. Thereafter, anti-frizz performance was evaluated in term of the volume of the hair tress, the higher the volume the weaker the anti-frizz performance. The end-capped sulfonated silicone (SCF2) exhibited better anti-frizz properties than the mixture of silicones (SCF1), silicone of Comparative Example 1 (SCF3) and no silicone (SCF4).

Hair styling formulations (HSFs) were prepared with an ionic silicone (I) (HSF1) and without silicones (HSF2 containing PVP-VA and HSF 3 containing water only as controls) as set forth in Table 14 below:

TABLE 14

Hair Styling Formulations With and Without End-Functionalized Ionic Silicone (I)

| Components | HSF 1 | HSF 2 | HSF 3 |
|---|---|---|---|
| Ionic Silicone of Example 3 | 0.5 | — | — |
| PVP-VA (BASF) | — | 0.5 | — |
| Water | 99.5 | 99.5 | 100 |

About 2.0 g of virgin curly hair tress was immersed in each HSF for 1 min and each wet hair tress was placed onto a curler stick which was then placed in an oven at 50° C. overnight. After 24 h, the hair tresses were removed from their sticks and placed vertically into a humidity chamber. Curl length was monitored at intervals of 15 min. The curl-length values were then plotted against time. The ionic silicone of Example 3 herein (HSF 1) retained the curl of the hair over a longer period of time that the controls (HSFs 2 and 3). Though the effectiveness of the ionic silicone (HSF1) was less than that of one of the best-known commercial materials (HSF2), hair treated with the former exhibited much better softness than the latter.

Several sunscreen formulations (SFs) were prepared and evaluated for sun protection. The SFs are set forth in Table 15 as follow:

TABLE 15

Sunscreen Formulations

| Phase | Components | SF1 | SF2 | SF3 |
|---|---|---|---|---|
| A | Deionized Water | 40.10 | 40.10 | 40.10 |
|   | Phenoxyethanol (and) Methylparaben (and) Isopropylparaben (and) Isobutylparaben (and) Butylparaben (Liquapar Optima, ISP) | 0.90 | 0.90 | 0.90 |
|   | SOLTERRA ™ Boost (Methylcellulose) | 2.00 | 2.00 | 2.00 |
| B | Methyl Glucose Sequistearate (Glucate SS, Noveon) | 1.00 | 1.00 | 1.00 |
|   | PEG 20 Methyl Glucose Sequistearate (Glucamate SSE 20, Noveon) | 1.00 | 1.00 | 1.00 |
|   | VP/Eicosene Copolymer (Ganex V220, ISP) | 2.00 |  |  |
|   | Ionic Silicone (I) of Example 3 |  | 2.00 |  |
|   | Ionic Silicone (I) of Example 7 |  |  | 2.00 |
|   | Cetearyl Alcohol (and) Ceteareth-20 (Lipowax D, Lipo Chemicals) | 3.00 | 3.00 | 3.00 |
|   | Low Lead Zinc Oxide Z-Cote ( ISP) | 25.00 | 25.00 | 25.00 |
|   | C12-15 Alkyl Benzoate | 25.00 | 25.00 | 25.00 |
| C | Citric Acid q.s. |  |  |  |
|   | Total | 100.00 | 100.00 | 100.00 |

To evaluate the sun protection factor (SPF) of SFs 1-3, a specific amount of each formulation was individually applied to artificial skin (pre-hydrated over 30% aqueous glycerin solution for 24 h) and dried at room temperature. The SPF of each film was measured using a UV-In Vitro SPF analyzer. The results are set forth in Table 16 as follows:

TABLE 16

SPF Measurements

|  | SF1 | SF2 | SF3 |
|---|---|---|---|
| In Vitro SPF | 3.2 ± 1.5 | 27.0 ± 4.9 | 17.2 ± 3.1 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

The invention claimed is:

1. A personal care composition comprising at least one personal care component and at least one end-functionalized ionic silicone wherein the silicone comprises at least two terminal ionic groups that form ionic aggregates, and where the ionic interactions have a reversible nature,
wherein the end-functionalized ionic silicone has the formula:

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ in which:
$R^1, R^2, R^3, R^5, R^6, R^8, R^9, R^{10}, R^{11}, R^{13}, R^{15}$ and $R^{16}$ each independently is an aliphatic, aromatic or fluoro monovalent hydrocarbon group having from 1 to 60 carbon atoms;

$R^4, R^{12}$ and $R^{17}$ each independently is a monovalent group bearing ion-pairs and having the formula -A-$I^{x-}M_n^{y+}$, or zwitterion having the formula —R'—$N^+(R'')_2$—R'''—$I^-$, in which A is a spacing moiety having at least one spacing atom, the spacing moiety being selected from the group consisting of divalent hydrocarbon group and hydrocarbonoxy group, I is an ionic group, R' is a divalent hydrocarbon group having from 1 to 20 carbon atoms, R'' is a monovalent hydrocarbon group having from 1 to 20 carbon atoms, R''' is a divalent hydrocarbon group having from 2 to 20 carbon atoms, and each M independently is hydrogen or a cation independently selected from alkali metals, alkali earth metals, transition metals, quaternary ammonium groups and phosphonium groups;

$R^7, R^{14}$ and $R^{18}$ each independently is —$CH_2CH(R^{19})$ $(C_nH_{2n})$—O—$(C_2H_4O)_o$—$(C_3H_6O)_p$—$(C_4H_8O)_q$—$R^{19}$ in which $R^{19}$ is hydrogen or an $R^1$ group as defined above;

superscripts x and y are positive integers subject to the limitation that x=ny;
each subscript n independently has a value of from 0 to 6 and subscripts o, p and q each independently has a value of from 0 to 1000, subject to the limitation that o+p+q≥1; and,
subscripts a, c, d, e, f, g, h, i and j each independently is zero or a positive integer subject to the limitations that 2≤a+b+c+d+e+f+g+h+i+j≤4500 and b≥2.

2. The personal care composition of claim 1 wherein in end-functionalized ionic silicone (I), each $R^1, R^2, R^3, R^5, R^6, R^8, R^9, R^{10}, R^{11}, R^{13}, R^{15}$ and $R^{16}$ group is independently selected from methyl, ethyl, n-propyl, iso-propyl, n-butyl, isobutyl, tert-butyl, n-pentyl, iso-pentyl, neopentyl, tert-pentyl, hexyl, heptyl, octyl, nonyl, decyl, cyclopentyl, cyclohexyl, cycloheptyl, methylcyclohexyl, naphthyl; tolyl, xylyl, ethylphenyl and benzyl.

3. The personal care composition of claim 1 wherein in end-functionalized ionic silicone (I), divalent spacing group A is an alkylene group $-(CHR^{20}-)_m$ wherein $R^{20}$ is hydrogen or an $R^1$ group and subscript m is a positive integer ranging from 1 to 100.

4. The personal care composition of claim 1 wherein in end-functionalized ionic silicone (I), divalent spacing group A is an arylene group selected from —$(CHR^{21})_k C_6 H_4$ $(CH_2)_r$— —$CH^2CH(R')(CH_2)_k C_6 H_4$— or —$CH_2CH(R^{22})$ $(CH_2)_r C_6 H_3 R^{23}$ wherein R' is hydrogen or an $R^1$ group, $R^{21}$ is hydrogen or an $R^1$ group, $R^{22}$ is hydrogen or an $R^1$ group, $R^{23}$ is a monovalent radical of from 1 to 20 carbon atoms and subscripts k and r are zero or positive integers subject to the limitation 0≤k+r≤100.

5. The personal care composition of claim 1 wherein in end-functionalized ionic silicone (I), divalent spacing group A is a hydrocarbonoxy group selected from $-(CHR^{24})_s-$ (O—$CHR^{24}CH_2)_{s'}$ and —O—$(CH_2-)_t$ wherein $R^{24}$ is hydrogen or an $R^1$ group, s has a value of from 0 to 50, s' has a value of from 1 to 50 and t has a value of from 0 to 50 subject to the limitation 1≤s+s'+t≤100.

6. The personal care composition of claim 1 wherein in end-functionalized ionic silicone (I), $I^-$ in the ion-pair-bearing group and in the zwitterion is selected from sulfonate —$SO_3^-$ and sulfate —$OSO_3$.

7. The personal care composition of claim 1 wherein in end-functionalized ionic silicone (I), $M^+$ is selected from Li, Na, K, Cs, Mg, Ca, Ba, Zn, Cu, Fe, Ni, Ga, Al, Mn, Cr, Ag, Au, Pt, Pd, Ru and Rh.

8. The personal care composition of claim 1 wherein in end-functionalized ionic silicone (I), in the zwitterion, R' is a divalent hydrocarbon radical having from 1 to 20 carbon atoms, R'' is a monovalent hydrocarbon radical having from 1 to 20 carbon atoms and R''' is a divalent hydrocarbon radical having from 2 to 20 carbon atoms.

9. The personal care composition of claim 1 wherein in end-functionalized ionic silicone (I), subscripts a, c, d, e, f, g, h, i and j each independently is zero or a positive number subject to the limitations that $2 \geq a+b+c+d+e+f+g+h+i+j \geq 4500$, $b>2$.

10. The personal care composition of claim 9 wherein in end-functionalized ionic silicone (I), subscript b is 2; subscripts a, c, e, f, g, h, i, j, k, l and m are 0; subscript d is from 5 to 1000, $R^5$, $R^6$, $R^{10}$ and $R^{11}$ are methyl or ethyl; $R^{10}$ is $-CH_2CH(H$ or $CH_3)-A-SO_3M$; A is a divalent benzyl radical; and, $M^+$ is Li, Na, K, Ag, a quaternary ammonium group, ammonium salt or phosphonium group.

11. The personal care composition of claim 1 wherein end-functionalized ionic silicone (I) is at least one of sodium sulfonate-capped polydimethylsiloxane, silver sulfonate-capped polydimethylsiloxane, magnesium sulfonate-capped polydimethylsiloxane, calcium sulfonate-capped polydimethylsiloxane, zinc sulfonate-capped polydimethylsiloxane and triethanolammonium sulfonate-capped polydimethylsilane.

12. The personal care composition of claim 1 further comprising at least one non-functionalized silicone.

13. The personal care composition of claim 1 further comprising at least one organic solvent.

14. The personal care composition of claim 1 formulated as an oil-in-water or water-in-oil emulsion.

15. The personal care composition of claim 1 wherein said personal care composition is selected from the group consisting of deodorants, antiperspirants, sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations thereof.

16. The personal care composition of claim 1 wherein said personal care composition is selected from the group consisting of deodorants, antiperspirants, sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations thereof.

* * * * *